(12) United States Patent
Gibbs et al.

(10) Patent No.: US 7,405,826 B2
(45) Date of Patent: Jul. 29, 2008

(54) SYSTEMS AND METHODS FOR CHIROPTICAL HETERODYNING

(76) Inventors: Phillip R. Gibbs, 6114 Park Ave. NE., Atlanta, GA (US) 30342-2349; Jason D. Beebe, 678 Somerset Ter., Apt. #10, Atlanta, GA (US) 30306

( * ) Notice: Subject to any disclaimer, the term of this patent is extended or adjusted under 35 U.S.C. 154(b) by 441 days.

(21) Appl. No.: 11/168,295

(22) Filed: Jun. 29, 2005

(65) Prior Publication Data
US 2006/0001876 A1 Jan. 5, 2006

Related U.S. Application Data

(60) Provisional application No. 60/584,105, filed on Jun. 30, 2004.

(51) Int. Cl.
*G01N 21/00* (2006.01)
*G01J 4/00* (2006.01)
(52) U.S. Cl. .................. 356/432; 356/364; 356/440; 356/368
(58) Field of Classification Search ......... 356/364–369, 356/432, 440; 250/225, 227.1, 252.1
See application file for complete search history.

(56) References Cited

U.S. PATENT DOCUMENTS

| 3,740,151 | A | 6/1973 | Chaney et al. |
| 4,011,451 | A | 3/1977 | Nelson |
| 4,276,475 | A | 6/1981 | Nelson |
| 4,498,774 | A | 2/1985 | Yeung et al. |
| 4,988,199 | A | * 1/1991 | Paul .......................... 356/368 |
| 5,168,326 | A | 12/1992 | Tokieda et al. |

(Continued)

FOREIGN PATENT DOCUMENTS

EP 0 438 465 7/1991

(Continued)

OTHER PUBLICATIONS

V. S. Zapasskii, "Depression of Excess Light Noise In Polarimetric Measurements," Opt. Spectrosc.(USSR) 47 (4), Oct. 1979, pp. 450-451.

(Continued)

*Primary Examiner*—L. G Lauchman
(74) *Attorney, Agent, or Firm*—Finnegan, Henderson, Farabow, Garrett & Dunner LLP

(57) ABSTRACT

An apparatus and method for improved detection of a chiral property of a sample begins with a probe beam of light having a first modulation frequency $\omega$ and is further modulated with a second modulation frequency $\phi$. A non-linear photo-detector, which may include multiple detector portions to form a balanced receiver, mixes the first modulation with the second modulation to analyze frequency components at inter-modulated sidebands, where the level of the inter-modulated sidebands are related to the chiroptical property of the sample. The inter-modulated sidebands may be the additive sidebands or the subtractive sidebands. A lock-in detector can be used to receive a signal output from the non-linear photo-detector and generate the modulation signals at the different modulating frequencies. Furthermore, the non-linear photo-detector may analyze a ratio of the inter-modulated sideband levels, such as $(\phi+2\omega)/(\phi+\omega)$, to yield a signal that is linearly related to the chiral property of the sample.

42 Claims, 9 Drawing Sheets

U.S. PATENT DOCUMENTS

| | | | |
|---|---|---|---|
| 5,209,231 | A | 5/1993 | Cote et al. |
| 5,276,376 | A | 1/1994 | Puskas |
| 5,286,941 | A | 2/1994 | Bel |
| 5,477,327 | A | 12/1995 | Bergman |
| 5,621,528 | A | 4/1997 | Rokos |
| 5,822,067 | A | 10/1998 | Yanik |
| 5,896,198 | A | 4/1999 | Chou et al. |
| 5,909,642 | A | 6/1999 | Suzuki |
| 6,046,805 | A * | 4/2000 | Kawamura et al. .......... 356/244 |
| 6,310,522 | B1 | 10/2001 | Wang et al. |
| 6,327,037 | B1 | 12/2001 | Chou et al. |
| 6,466,320 | B1 | 10/2002 | Kawamura et al. |
| 6,574,022 | B2 | 6/2003 | Chow et al. |
| 6,661,297 | B2 | 12/2003 | Pepper |
| 6,885,882 | B2 * | 4/2005 | Cote et al. .................. 600/319 |
| 2003/0098746 | A1 | 5/2003 | Aikawa et al. |
| 2004/0046613 | A1 | 3/2004 | Wissell |
| 2004/0070766 | A1 | 4/2004 | Szafraniec |
| 2005/0128482 | A1 * | 6/2005 | Gibbs ......................... 356/364 |

FOREIGN PATENT DOCUMENTS

| | | |
|---|---|---|
| EP | 0 905 506 | 3/1999 |
| EP | 1 065 497 | 1/2001 |
| EP | 1 096 248 | 5/2001 |
| EP | 1 231 455 | 8/2002 |
| EP | 1 253 715 | 10/2002 |
| EP | 0 805 352 | 3/2003 |
| JP | 2002 190780 | 7/2005 |
| WO | WO 01/06918 | 2/2001 |
| WO | WO 02/25235 | 3/2002 |
| WO | WO 03/029790 | 4/2003 |

OTHER PUBLICATIONS

V. S. Zapasskii, "High-Sensitivity Polarimeter Based on the ILA-120 Argon Laser," Opt. Spectrosc. (USSR) 52(6), Jun. 1982, pp. 667-669.

Jonathan D. Spear and Richard E. Russo, Low Noise Position Sensitive Detector for Optical Probe Beam Deflection Measurements, Rev. Sci. Instrum., vol. 67, No. 7, Jul. 1996, pp. 2481-2484.

D. Chauvat, J. Guena, Ph. Jacquier, M. Lintz, M. A. Bouchiat, M.D. Plimmer and C.W. Goodwin, "Magnification of a Tiny Polarisation Rotation by a Dichroic Plate in Balanced Mode Polarimetry," Optics Communications 138, Jun. 1, 1997, pp. 249-252.

Alfredo Arnaud, Fernando Silveira, Erna M. Frins, Alfredo Dubra, César D. Perciante, and José A. Ferrari, "Precision Synchronous Polarimeter with Linear Response for the Measurement of Small Rotation Angles," Applied Optics, vol. 39, No. 16, Jun. 1, 2000, pp. 2601-2604.

L. A. Barragán, J. I. Artigas, R. Alonso and F. Villuendas, "A Modular, Low-cost, Digital Signal Processor-Based Lock-in Card for Measuring Optical Attenuation," Rev. Sci. Instrum., vol. 72, No. 1, Jan. 2001, pp. 247-251.

Aloke Jain, Jayant Kumar, Fumin Zhou, Lian Li and Sukant Tripathy, "A Simple Experiment for Determining Verdet Constants Using Alternating Current Magnetic Fields," Am. J. Phys., vol. 67, No. 8, Aug. 1999, pp. 714-717.

K. Turvey, "Determination of Verdet Constant from Combined Ac and Dc Measurements," Rev. Sci. Instrum., vol. 64, No. 6, Jun. 1993, pp. 1561-1568.

Charles A. Goss, Douglas C. Wilson, and William E. Weiser, "Flow Injection Analysis with High-Sensitivity Optical Rotation Detection," Anal. Chem. vol. 66, No. 19, Oct. 1, 1994, pp. 3093-3101.

Hirofumi Kawazumi, Hideki Nishimura, Yukiaki Otsubo and Teiichiro Ogawa, "Universal On-Line Detector For High-Performance Liquid Chromatography Via Magneto-Optical Rotation," Talanta, vol. 38, No. 9, 1991, pp. 965-969.

J. Koch, A. Zybin, and K. Niemax, "Narrow and Broad Band Diode Laser Absorption Spectrometry— Concepts, Limitations and Applications," Spectrochimica Acta Part B 57 (2002) pp. 1547-1561.

Vladimir Liger, Alexander Zybin, Yurii Kuritsyn, and Kay Niemax, "Diode-Laser Atomic-Absorption Spectrometry by the Double-Beam-Double-Modulation Technique," Spectrochimica Acta Part B 52 (1997) pp. 1125-1138.

Rongjun Wang, Yangqin Chen, Peipei Cai, Jingjing Lu, Zhiyi Bi, Xiaohua Yang and Longsheng Ma, "Optical Heterodyne Velocity Modulation Spectroscopy Enhanced by a Magnetic Rotation Effect," Chemical Physics Letters 307 (1999) pp. 339-342.

Norman P. Barnes and Larry B. Petway, "Variation of the Verdet Constant With Temperature of Terbium Gallium Garnet," J. Opt. Soc. Am. B, vol. 9, No. 10, Oct. 1992, pp. 1912-1915.

E. J. Gillham, "A High-Precision Photoelectric Polarimeter," Journal of Scientific Instruments, vol. 34, Nov. 1957, pp. 435-439.

Z. P. Wang, Q. B. Li, R.Y. Feng, H. L. Wang, Z. J. Huang, and J. H. Shi, "Effects of the Polarizer Parameters upon the Performance of an Optical Current Sensor," Optics & Laser Technology 36, 2004, pp. 145-149.

P. G. L. Mills and M. O. J. Hawksford, "Transconductance Power Amplifier Systems for Current-Driven Loudspeakers," J. Audio Eng. Soc., vol. 37, No. 10, Oct. 1989, pp. 809-822.

James Karki, "Voltage Feedback Vs. Current Feedback Op Amps," Literature No. SLVA051, Nov. 1998, pp. 1-10, A-1-6.

Debbie Brandenburg, "Current vs. Voltage Feedback Amplifiers," National Semiconductor Corporation, Jan. 1998, pp. 1-6.

Debbie Brandenburg, "Current vs. Voltage Feedback Amplifiers,"2002 National Semiconductor Corporation, OA-30, Jan. 1998, pp. 1-5.

Arne Buck, "Current-Feedback Myths Debunked," 2002 National Semiconductor Corporation OA-20, Jul. 1992, pp. 1-4.

Daniel A. DeAntonio, "Soft Magnetic Ferritic Stainless Steels," Advanced Materials & Processes, Oct. 2003, pp. 29-32.

Carlo Bertucci, Vincenza Andrisano, Vanni Cavrini and Ettore Castiglioni, "Reliable Assay of Extreme Enantiomeric Purity Values by a New Circular Dichroism Based HPLC Detection System," Chirality 12:84-92 (2000).

Prasad L. Polavarapu, "Optical Rotation: Recent Advances in Determining the Absolute Configuration," Chirality 14:768-781, 2002.

M. Bouchiat, D. Chauvat, J. Guéna, Ph. Jacquier, M. Lintz, and M. D. Plimmer, "High Precision Balanced Mode Polarimetry With a Pulsed Laser Beam," Optics Communications 119, Sep. 1, 1995 pp. 403-414.

Timothy W. King, Gerard L. Coté, Roger McNichols, Marcel J. Goetz, Jr., "Multispectral Polarimetric Glucose Detection Using a Single Pockets Cell," Optical Engineering, vol. 33, No. 8 Aug. 1994, pp. 2746-2753.

"The Benefits of DSP Lock-In Amplifiers," Optronic Laboratories, Inc., Application Note (A12), Revision A, Sep. 1996, pp. 1-8.

"Lock-In Amplifiers"225.02 Bentham Instruments Ltd., pp. 1-10.

Application Note #3, "About Lock-In Amplifiers", Stanford Research Systems, pp. 145-155.

Donald R. Bobbit, and Sean W. Linder, "Recent Advances in Chiral Detection For High Performance Liquid Chromatography," Trends In Analytical Chemistry, vol. 20, No. 3, 2001, pp. 111-123.

H. J. Lozykowski, T. Li and Z. I. Akir, "Digital Spectropolarimeter For The Measurement of Optical Polarization," Rev. Sci. Instrum., vol. 63, No. 9, Sep. 1992, pp. 4096-4101.

M. Bouchiat, D. Chauvat, J. Guèna, Ph. Jacquier, M. Lintz, and M. D. Plimmer, "High Precision Balanced Mode Polarimetry With a Pulsed Laser Beam," Optics Communications, 119, Sep. 1, 1995, pp. 403-414.

D. Chauvat, J. Guèna, Ph. Jacquier, M. Lintz, M.A. Bouchiat, M. D. Plimmer and C. W. Goodwin, "Magnification of a Tiny Polarisation Rotation By a Dichroic Plate in Balanced Mode Polarimetry," Optics Communications 138, Jun. 1, 1997, pp. 249-252.

Andreas Mandelis, Stefano Paoloni and Lena Nicolaides, "Novel Lock-In Waveform Technique for Signal-to-Noise Ratio and Dynamic-Range Enhancement in Highly Noised Photothermal Experiments," Analytical Sciences, vol. 17, Apr. 2001, pp. s5-s8.

Roger J. McNichols, Gerard L. Coté, Marcel J. Goetz, Jr., and Timothy W. King, "Linear Superposition of Specific Rotation for the Detection of Glucose" IEEE, 1993, pp. 1549-1550.

Aidan F. Browne, Todd R. Nelson and Robert B. Northrop, "Microdegree Polarimetric Measurement of Glucose Concentrations for Biotechnology Applications," IEEE, 1997, pp. 9-10.

Sunghoon Jang, Zhi Yang, Martin D. Fox and Dan Censor, "Double Lock-In Amplifier Faraday Rotation Glucometer," IEEE 2000, pp. 107-108.

Marcel J. Goetz, Jr., Martin D. Fox, MD. Ph.D, and Robert B. Northrop, Ph.D, "Microdegree Polarimetry Using A Diode Laser For Glucose Detection," IEEE, 1992, pp. 97-98.

Sunghoon Jang, and Martin D. Fox, "Double Lock-In Concept For More Glucose Detection," IEEE, 1999, pp. 122-124.

Michael La Marca, "Laser Interferometer Gravitational Wave Observatory," California Institute of Technology. Massachusetts Institute of Technology, Surf Final Report, Sep. 7, 2001, pp. 1-17.

C. Denise Caldwell, "Digital Lock-In Technique For Measurement of Polarization of Radiation," Optics Letters, vol. 1, No. 3, Sep. 1977, pp. 101-103.

Harry G. Brittain, "Applications of Chiroptical Spectroscopy for the Characterization of Pharmaceutical Compounds," Journal of Pharmaceutical and Biomedical Analysis 17, 1998, pp. 933-940.

"FM Spectroscopy with Tunable Diode Lasers" Application Note 7, New Focus, 2001, pp. 1-11.

Dr. Theodore Oakberg, "Linear Birefringence and Optical Rotation," PEM- 90 Application Note, Hinds Instruments, Inc., 1993, pp. 1-6.

Roger J. McNichols, Brent D. Cameron and Gerard L. Coté, "Development of a Non-Invasive Polarimetric Glucose Sensor," IEEE, Apr. 1998, pp. 1-3.

XP-001121554, Chien Chou, Yen-Chuen Haung, Ching-Mei-Feng and Ming Chang, "Amplitude Sensitive optical Heterodyne and Phase Lock-in Technique on Small Optical Rotation Angle Detection of Chiral Liquid", Jpn. J. Appl. Phys., vol. 36, Jan. 1997, pp. 356-359.

E. A. Avrutin, J. H. Marsh and E. L. Portnoi, "Monolithic and Multi-GigaHertz Mode-Locked Semiconductor Lasers: Constructions, Experiments, Models and Applications", IEE-Proc.-Optoelectron., vol. 147, No. 4, Aug. 2000, pp. 251-278.

Fabrizio Barone, Enrico Calloni, Luciano Difiore, Aniello Grado, Leopoldo Milano & Guido Russo, "High-Performance Modular Digital Lock-in Amplifier", Rev. Sci. Instrum. vol. 66 No. (6), Jun. 1995, American Institute of Physics pp. 3697-3702.

Co-pending U.S. Appl. No. 11/120,723, Title: A Double Reference Lock-In Detector, Inventor: Phillip R. Gibbs, filed May 3, 2005.

Co-pending U.S Appl. No. 11/168,296, Title: Systems and Methods for Automated Resonant Circuit Tuning, Inventor: Phillip R. Gibbs, filed Jun. 29, 2005.

V. McOmber, "Swept Coherent-heterodyne Techniques Provide High Resolution,"— XP-001208118, Laser Focus World, vol. 38, No. 5, May 2002, pp. 173-178.

International Search Report dated Nov. 23, 2005, for PCT/US2005/022893.

Stanford Research Systems, "About Lock-In Amplifiers" Application #3.

Alfredo Arnaud, Fernando Silveira, Ema M. Frins, Alfredo Dubra, César D. Perciante, and José A. Ferrari, "Precision Synchronous Polarimeter with Linear Response for the Measurement of Small Rotation Angles," Applied Optics, vol. 39, No. 16, Jun. 1, 2000, pp. 2601-2604.

Glenn A. Laguna, "Source Noise Reduction in Diode Laser Spectroscopy Using the Faraday Effect," Applied Optics, vol. 23, No. 13, Jul. 1, 1984, pp. 2155-2158.

José A. Ferrari, César D. Perciante, Alejandro Lagos, and Ema M. Frins, "Improved Method for Faraday Current Sensor Data Processing," Optics Communications, 199 (2001) pp. 77-81.

José A. Ferrari, César D. Perciante, Alfredo Dubra, Alfredo Arnaud, and Ema M Frins, "Alternating Current Sensor With Second-Harmonic Detection," Applied Optics, vol. 39, No. 25, Sep. 1, 2000, pp. 4638-4640.

José A. Ferrari, Alfredo Debra, Alfredo Arnaud, and Daniel Perciante, "Current Sensor Using Heterodyne Detection," Applied Optics, vol. 38, No. 13, May 1, 1999, pp. 2808-2811.

Jonathan D. Spear, and Richard E. Russo, "Low Noise Position Sensitive Detector For Optical Probe Beam Deflection Measurements," Rev. Sci. Instrum., vol. 67, No. 7, Jul. 1996, pp. 2481-2484.

P. G. L. Mills and M. O. J. Hawksford, "Distortion Reduction in Moving-Coil Loudspeaker Systems Using Current-Drive Technology," J. Audio Eng. Soc., vol. 37, Mar. 1989, pp. 129-148.

W. L. L. Lenders, "The Orthocyclic Method of Coil Winding," Philip Technical Review, vol. 23, No. 12, Oct. 16, 1962, pp. 365-404.

"Lock-In Amplifiers" Bentham Instruments Ltd., pp. 1-10.

Application Note #3, "About Lock-In Amplifiers", pp. 145-155.

Peter Rozea, "Chiral Compound Analyses and Faraday Polarimetry" Application Note, Nov. 2001, pp. 20-23.

M. G. Finn, "Emerging Methods for the Rapid Determination of Enantiomeric Excess," Chirality 14:534-540, 2002.

Brent D. Cameron and Gerard L. Coté, "Polarimetric Glucose Sensing in Aqueous Humor Utilizing Digital Closed-Loop Control," 18th Annual International Conference of the IEEE Engineering In Medicine and Biology Society, Amsterdam 1996, pp. 204-205.

H. J. Lozykowski, T. Li, and Z. I. Akir, "Digital Spectropolarimeter for the Measurement of Optical Polarization," Rev. Sci. Instrum., vol. 63, No. 9, Sep. 1992, pp. 4096-4101.

M. Bouchiat, D. Chauvat, J. Guena, Ph. Jacquier, M. Lintz and M. D. Plimmer, "High Precision Balanced Mode Polarimetry with a Pulsed Laser Beam," Optics Communications 119, Sep. 1, 1995, pp. 403-414.

Vladimir Liger, Alexander Zybin, Yurii Kuritsyn and Kay Niemax, "Diode-Laser Atomic-Absorption Spectrometry by the Double-Beam-Double-Modulation Technique," Spectrochimica Acta Part B 52 1997, pp. 1125-1138.

Jonathan D. Spear and Richard E. Russo, "Low Noise Position Sensitive Detector For Optical Probe Beam Deflection Measurements," Rev. Sci. Instrum., vol. 67, No. 7, Jul. 1996, pp. 2481-2484.

International Search Report dated Aug. 29, 2005, for PCT/US2005/015312 (corresponding to the present application).

International Search Report dated Sep. 27, 2005 for 9524.008-304 (corresponding to U.S. Appl. No. 11/168,296).

Co-pending U.S. Appl. No. 11/168,295, Title: Systems and Methods for Chiroptical Heterodyning, Inventors: Phillip R. Gibbs et al., filed Jun. 28, 2005.

* cited by examiner

SYSTEMS AND METHODS FOR CHIROPTICAL HETERODYNING

RELATED APPLICATIONS

The present application hereby claims the benefit of U.S. Provisional Patent Application Ser. No. 60/584,105, which was previously filed by the same inventors on Jun. 30, 2004.

DESCRIPTION OF THE INVENTION

1. Field of the Invention

This invention relates to systems for optical detection and, more particularly, to systems and methods using a non-linear detector to mix a large optical modulation signal and a weak chiroptical signal of interest at a photodetector enabling analysis of the received optical inter-modulation sidebands for an enhanced and more sensitive detection scheme.

2. Background of the Invention

In general, a "chiral" object is one that is not superimposable upon its mirror image. In other words, a chiral object and its mirror image are similar in constitution or content, but different in orientation. Examples of chiral objects include a human hand, a mechanical screw, or a propeller. While they the mirror images look similar, they have different characteristic orientations with regard to their parts (e.g., the digits on the hand, the helical orientation of the screw, and the pitch orientation of the blades on the propeller).

In stereochemistry, two forms of a chiral object (such as a molecule) are also known as enantiomers, which is a type of stereoisomer. Enantiomers have the same chemical purity (e.g., the same mass, absorbance, refractive index, Verdet constant, etc.) but have different configurations in symmetry or symmetric properties. A collection containing only one enantiomeric form of a chiral molecule is often referred to as enantiopure, enantiomerically pure, or optically pure. However, unlike other stereoisomers, enantiomers are often difficult to separate and quantitate.

Detection of chiral molecules has become of increasing interest to the pharmaceutical industry over the last twenty years. This interest is driven at least in part by the common occurrence of drastically different pharmacological activities between enantiomers. The different pharmacological activity associated between enantiomers often requires that the drug be produced as a single chiral isomer. This single chiral isomer would be selected as it would have the most beneficial effects or, in some cases, would not have dangerous pharmacological activity. However, analytical methods for assaying enantiomeric purity have not kept pace with the increasing demands for rapid, high sensitivity, enantiomeric analysis.

Currently, chiral separation of the enantiomers and individual quantification of the chiral species is a commonly used technique for assaying enantiomeric purity. A direct non-contact method of assaying enantiomeric purity would be preferred and increased sensitivity over the ~99.5% enantiomeric excess (ee) limit is needed. Several optical properties unique to chiral molecules have been utilized in techniques such as polarimetry, optical rotatory dispersion, and circular dichroism. However, known quantification techniques utilizing such optical properties lack the sensitivity to detect pharmacologically relevant levels of enantiomeric impurities in many desired modern pharmaceuticals.

One example of an improved method for detecting pharmacologically relevant levels of enantiomeric impurities utilizes a modulated light passed through a magnetically modulated sample cell. The modulated light from the sample cell is then optically detected. This improved method is disclosed in International Patent Application No. PCT/US02/31279 entitled "HIGH-THROUGHPUT CHIRAL DETECTOR AND METHODS FOR USING SAME." Of particular interest in the present application is an improvement on how to detect the modulated light to improve sensitivity of the detecting apparatus as a whole.

Previous work has utilized heterodyne interference to improve polarimetric detection of a probe beam. (U.S. Pat. No. 6,327,037 by Chou, et al. and entitled "Optical Rotation Angle Polarimeter"; U.S. Pat. No. 5,896,198 by Chou et al. and entitled "Optical Heterodyne-based Method and Apparatus for Determining the Concentration of Optically Active Substances"; U.S. Patent Application #20020180979 by Chou, et al. and entitled "Optical Heterodyne Surface Plasma Wave Detecting Method and Apparatus"; and U.S. Patent Application #20040070766 by Szafraniec, Bogdan and entitled "Method and Apparatus for a Jones Vector Based Heterodyne Optical Polarimeter"). However, the disclosed methods and systems in accordance with embodiments of the present invention utilize fundamentally different heterodyning techniques (e.g., it does not rely upon using a two higher frequencies from a laser source that are down-converted for baseband processing). Furthermore, these previous methods essentially only utilized the frequency selectivity of heterodyne signals as opposed to any optical gain capabilities of the technique.

Thus, there is a need for an improved system and method for optical detection by mixing of a large optical modulation and a weak chiroptical signal of interest occurs at a nonlinear detector (e.g., square law detector) to yield inter-modulated sidebands, which are dependent upon the chiroptical property of interest with a large signal gain and yielding more sensitive detection and more information than previous methods.

SUMMARY OF THE INVENTION

In accordance with the invention, a system and method are disclosed to yield more sensitive detection of a chiroptical property of a sample. Generally, the invention uses a non-linear detector to mix optical modulation with system polarization modulation and analyze at inter-modulated sidebands for concentration and optical activity parameter measurements. In other words, a non-linear detector is used to mix a large optical modulation signal and a weak chiroptical signal of interest at a photodetector enabling analysis of the received optical inter-modulation sidebands for an enhanced and more sensitive detection scheme.

According to one aspect of the present invention, an improved apparatus and method for detection of a chiral property of a sample is described. First, a probe beam of light has a first modulation frequency w and is further modulated with a second modulation frequency $\phi$. A non-linear photodetector, which may include multiple detector portions to form a balanced receiver, mixes the first modulation with the second modulation to analyze frequency components at inter-modulated sidebands, where the level of the inter-modulated sidebands are related to the chiroptical property of the sample. The inter-modulated sidebands are preferably the additive sidebands, but may include subtractive ones as well. A lock-in detector can be used to receive a signal output from the non-linear photo-detector and generate the modulation signals at the different modulating frequencies. Furthermore, the non-linear photo-detector may analyze a ratio of the inter-modulated sideband levels, such as $(\phi+2\omega)/(\phi+\omega)$, to yield a signal that is linearly related to the intrinsic chiralty of the sample (i.e. enantiomeric excess, ee %).

It is to be understood that both the foregoing general description and the following detailed description are exemplary and explanatory only and are not restrictive of the invention, as claimed. Advantages of aspects of the invention may be set forth in part in the description which follows, and in part will be obvious to one skilled in the art from the description, or may be learned by practice of embodiments of the invention.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present exemplary embodiments of the invention, examples of which are illustrated in the accompanying drawings, presentations, specifications and other technical documentation. Wherever possible, the same reference numbers will be used throughout the drawings to refer to the same or like parts.

Figure 1:
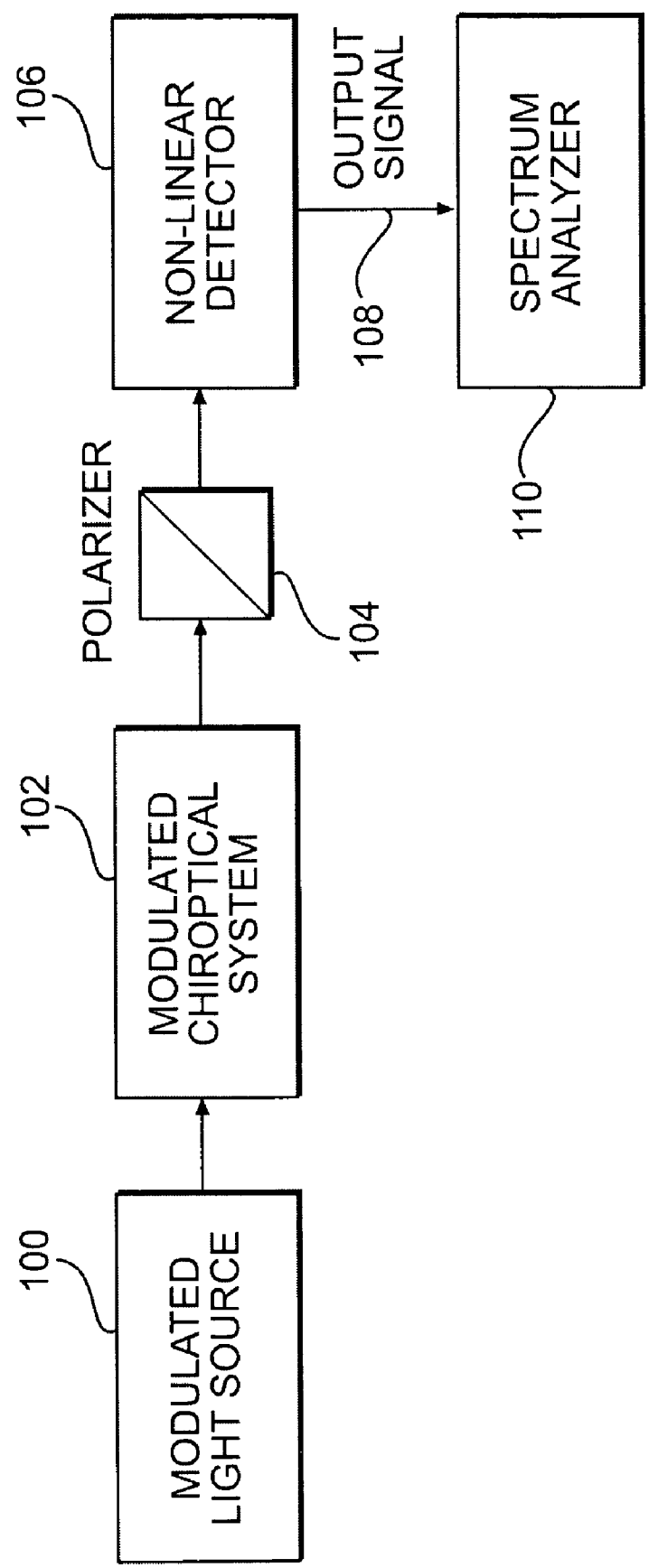
FIG. 1 is an exemplary block diagram of a chiroptical heterodyning system in accordance with an embodiment of the present invention.

In general, FIG. 1 illustrates an exemplary chiroptical heterodyning system according to an embodiment of the present invention. Referring now to FIG. 1, the system has a light source 100, a chiroptical system 102, a polarizer 104, a detector 106, and a spectrum analyzer 110 as generally shown in FIG. 1. The light source 100 provides the probe into the system 102 for detecting a response at the detector 106. A high intensity monochromatic light source such as a laser is preferred as light source 100 but other types of light sources (e.g., a tungsten lamp, a xenon flash lamp, etc.) coupled with wavelength selectors (acousto-optical tunable filters, monochromators, etc.) would also work suitably as light source 100.

In the embodiment shown in FIG. 1, light source 100 is modulated. The modulation can be accomplished by modulating the light intensity, wavelength, or polarization state of the input beam probing the chiroptical system (i.e., w). The modulation is ideally a sine wave, but it is possible to use other types of modulation signals in other embodiments of the invention. For example, the light source 100 may be pulsed by a square wave modulation signal when the detector is inherently band limited to reject the unwanted higher order signals generated from the square wave signal's modulation spectrum. Thus, those skilled in the art will quickly appreciate that the selection of the type and rate of modulation will be an empirical choice selected by the system designer based upon parameters of the system's implementation.

The chiroptical system 102 is shown in FIG. 1 to be modulated as well. In one embodiment, the system 102 is modulated preferably using one of several known induced optical effects (i.e., magneto-optic [Faraday effect, Voigt effect, Cotton-Mouton effect], electro-optic [Kerr effect, Pockels effect] or photoelasticity to modulate system 102 directly at a frequency distinct from the modulated probe beam (i.e., $\phi$).

The transmitted light of the modulated probe beam exits a sample cell (not shown) within chiroptical system 102 and passes through an analyzing polarizer element 104 (e.g., a Nicol prism, a Glan-Laser polarizer, a Glan-Thompson polarizer, Glan-Foucault polarizer, Wollaston prism, Rochon prism, etc.). The transmitted light from polarizer 104 hits a non-linear detector 106, such as a square law detector (e.g., photodiode, avalanche photodiode, photomultipler tube, etc.) where the light is turned into an electronic signal 108. The two modulation frequencies mix at the detector 106 and produce inter-modulated sidebands in the electronic output signal 108. The frequency spectrum of the output signal 108 may then be visually observed via a spectrum analyzer 110, which shows the observer the amplitude of different frequency related components (such as the level of signals at particular inter-modulated frequencies) making up signal 108. In the case of absorptive chiroptical effects, such as circular dichroism, the exiting polarizer element 104 may be omitted.

Observing chiroptical dependent signals at the inter-modulated sideband frequencies has several advantages in addition to the large gain imparted to the weak chiroptical signal at the fundamental frequency $\phi$. First, observation at the sideband frequencies allows one to avoid noise at either of the driving frequency fundamentals (i.e., $\omega$ and $\phi$), which tend to be noisy due to pickup in the system electronics. Secondly, whereas modern telecommunications routinely use super-heterodyning to down modulate high frequency signals for easier analysis (e.g., $\phi-\omega$), the additive sidebands in an embodiment of the present invention can also be utilized to obtain higher modulation rates than one could readily obtain in certain chiroptical systems (e.g., Faraday rotation). Therefore, these additive sidebands can further improve rejection of 1/f noise that typically plagues analytical measurements by allowing observation at higher frequencies via other techniques (e.g., lock-in detection, synchronous detection, double lock-in detector (such as that disclosed in U.S. Provisional U.S. Patent Application Ser. No. 06/568,104, entitled "Double Reference Lock-in Detector" by Phillip R. Gibbs)). In addition, direct modulation of the chiroptical system 102 is the preferred mode of utilizing lock-in analysis for signal recovery because the signals of interest (i.e., natural and induced optical activity) are directly modulated introducing less noise into the measured properties of interest.

There are several classes of chiroptical heterodyning systems that implement embodiments of the present invention. The first type utilizes direct modulation of the input light amplitude coupled with another device to modulate a chiroptical property of the beam to probe a sample containing a chiral species. These systems represent a simpler modification to existing techniques of chiroptical analysis.

A second class of chiroptical heterodyning systems modulates the input light amplitude and directly modulates the chiroptical properties of the sample cell. In general, the direct modulation of the system of interest (in this case the sample chamber containing the chiral species) may be preferred as it may provide better or a more optimum noise rejection when detecting chiroptical properties of the analyte.

A third class of chiroptical heterodyning systems modulates a chiroptical property of the input probe beam (e.g., linear polarization state) and separately modulates a chiroptical property of the system containing the sample. These systems are preferred for the best noise rejection because these systems have the highest RMS optical power and maximize optical gain. Several examples of each of these types of systems are described with magneto-optic, electro-optic, acousto-optical, and photoelastic modulation.

Figure 2:
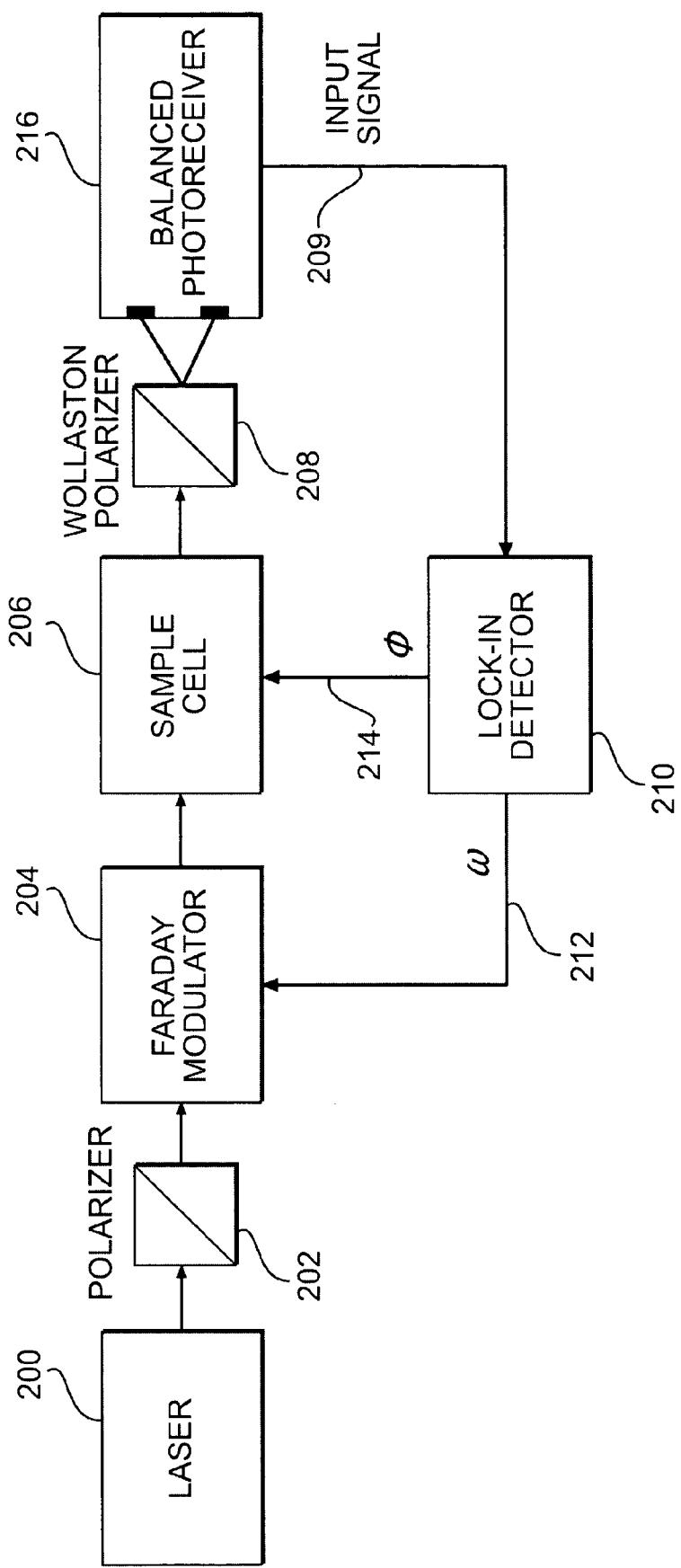
FIG. 2 is an exemplary diagram illustrating a prototype modified MOPED apparatus in accordance with an embodiment of the present invention.

Looking at these types or classes of chiroptical heterodyning systems in more detail, FIG. 2 illustrates an example of an analytical instrument utilizing chiroptical heterodyning in accordance with an embodiment of the invention. This can be termed a modified Magneto-Optical Enantiomeric Detector or MOPED apparatus. Referring now to FIG. 2, a laser 200 generates a probe beam of light provided to a polarizer 202. Thereafter, the input linear polarization state of the probe beam is modulated with a Faraday modulator 204 by signal 212 at a frequency of w. In an alternative embodiment, the Faraday modulator 204 may be placed after the sample cell 206 instead of being before the sample cell 206). The sample cell 206 is a device for holding the sample analyte while being exposed to further modulation. In one embodiment, the sample cell 206 holds analytes suspended in a solvent while the probe beam is applied through the sample cell (and analytes in the solvent) while additional modulation is applied to the probe beam. In the illustrated embodiment, the sample cell 206 is directly modulated in an analogous manner (Faraday rotation) yielding modulated chiroptical signals dependent on the Verdet constant and natural optical activity of the sample modulated by signal 214 at a frequency of φ.

Analyzing polarizer 208 receives the resulting probe beam from the sample cell 206, but is not a focusing lens or other optical focusing element. Instead, polarizer 208 splits up the beam into two diverging parts. In one embodiment, the analyzing polarizer 208 is a Wollaston polarizer, which yields two inversely coupled signal beams orthogonal to each other. The beams come out of polarizer 208 and are intercepted by two photo-detectors placed in front of the beams within a balanced photo-receiver 216. Observing these two beams using the photo-detectors in photo-receiver 216 yields a square law detector with a high common-mode rejection ratio (CMRR). In the illustrated embodiment, the driving frequencies φ and ω are synchronized with the lock-in internal reference, such as a voltage controlled oscillator (not shown) or a signal synthesizer (not shown) within lock-in detector 210, for accurate phase determination on the sidebands.

When the analyzing polarizer 208 is set so that one beam is at null relative to the input polarization, those skilled in the art will appreciate that the analysis of the resulting inter-modulated signals yields frequencies that are linearly dependent on the Verdet constant of the sample (i.e., φ+ω) and frequencies that are linearly dependent on the natural optical activity a (i.e., (φ+2ω). Both of these types of signals provide useful analytical information to the researcher. When the analyzer is set so that one beam is at 45° relative to the input polarization, analysis of the resulting inter-modulated signals still yields frequencies that are dependent on the Verdet constant and on of the natural optical activity, a, of the sample but the relation is reversed (i.e., φ+2ω is now linearly dependent on Verdet). The frequency relationships of the sidebands to Verdet and optical activity at the 45° and null are shown below in Table 1 & 2.

TABLE 1

Inter-modulated sideband dependence at 45° analyzer setting.

| | ω | 2ω | 3ω | 4ω | 5ω |
|---|---|---|---|---|---|
| Φ | alpha | verdet | alpha | verdet | alpha |
| 2Φ | verdet | alpha | verdet | alpha | verdet |
| 3Φ | alpha | verdet | alpha | verdet | alpha |
| 4Φ | verdet | alpha | verdet | alpha | verdet |
| 5Φ | alpha | verdet | alpha | verdet | alpha |

TABLE 2

Inter-modulated sideband dependence at null analyzer setting.

| | ω | 2ω | 3ω | 4ω | 5ω |
|---|---|---|---|---|---|
| Φ | verdet | alpha | verdet | alpha | verdet |
| 2Φ | alpha | verdet | alpha | verdet | alpha |
| 3Φ | verdet | alpha | verdet | alpha | verdet |
| 4Φ | alpha | verdet | alpha | verdet | alpha |
| 5Φ | verdet | alpha | verdet | alpha | verdet |

Tables 3 & 4 shown below illustrate an example of the intermodulated sideband dependence when the laser power is modulated. In the embodiment exemplified in Table 4, the fundamental frequency from the laser modulation is only dependant on laser power intensity and is the result of a non-ideal extinction coefficient in the polarizers. This fact can be utilized to normalize the optical rotation (e.g., f+w, f−w) and Verdet signal (e.g., 2f+w, 2f−w) for power fluctuations in the laser beam that show up as multiplicative noise in the recovered signals. The log ratio of these the signals and the power measure at w can be utilized for reduction of multiplicative noise by post processing in the DSP.

TABLE 3

Inter-modulated sideband dependence with laser power modulation, at 45° analyzer setting.

| | polarizers 45 | | |
|---|---|---|---|
| laser mod (w) | 0 | w | 2w |
| 0 | 0 | alpha | 0 |
| f | verdet | verdet | 0 |
| 2f | alpha | alpha | 0 |

TABLE 4

Inter-modulated sideband dependence with laser power modulation at null analyzer setting.

| | polarizers 90 | | |
|---|---|---|---|
| laser mod (w) | 0 | w | 2w |
| 0 | 0 | laser power | 0 |
| f | alpha | alpha | 0 |
| 2f | verdet | verdet | 0 |

To obtain the response shown above in Table 4, it may be desired to use another polarizer (not shown in FIG. 2) prior to the Wollaston polarizer 208 in the optical path. In this manner, the Wollaston polarizer 208 is still used as a 45 degree split for CMRR, but responds as if being observed at a null.

An exemplary mode of operation is to operate with one of the sample beams set to null relative to the input polarizer. Under these conditions, the fundamental frequency contributions to the signal output (i.e., $\omega$ and $\phi$ in the example of FIG. 2) from the photoreceiver 216 disappear and any harmonic distortion on the modulator coils in the sample cell 206 is advantageously eliminated from contributing to the detector output signal. Thus, the relatively large optical modulation is removed as the predominant signal in the output signal leaving the second harmonic of the optical modulation as the dominant signal in the output signal's frequency spectrum. This signal can be utilized to normalize the influence of light intensity fluctuations on other signals of interest.

Of the inter-modulation signals available at the null polarizer angle, ($\phi+\omega$ and $\phi+2\omega$ are the strongest signals of interest and are preferred over utilizing the subtractive sidebands ($\phi-\omega$ and $\phi-2\omega$) due to the higher modulation rate. An additional benefit of the modified MOPED device shown in FIG. 2, is that no moving parts are required. Absorptive centers are not necessary for the manifestation of Verdet or natural optical activity, so this technique is broadly applicable to chemical species previously difficult for conventional techniques (e.g., carbohydrates, weak optical activity, low ee %, high ee contaminants >99.5 ee %).

One potential complication for accurate observation of small changes in Verdet signals due to a chemical species of interest can be the relatively large background from the solvent. This large background signal can be removed prior to the lock-in analysis of the signal due to the analyte by a process analogous to active noise cancellation and this process is subject of a separate U.S. Provisional Patent Application entitled "Active Single Frequency Background Taring for Magneto-Optical Analysis", which was concurrently filed with the present application and which is hereby fully incorporated by reference. Thus, at the null setting, a new parameter $\phi'+\omega'$ is utilized for changes in the Verdet constant relative to the solvent, where the contribution from the solvent is effectively zeroed. Therefore, the ratio of ($\phi+2\omega/\phi'+\omega'$)×(phase of $\phi+2\omega$) is linearly related to changes in the ee % of the sample because the optically dependent signal ($\phi+2\omega$) is normalized for concentration changes ($\phi'+\omega'$).

This ratio is an intrinsic property and independent of light intensity fluctuations from the light source since both signals, $\phi+2\omega$ and $\phi'+\omega'$, are linearly dependent on light intensity. As the ratio is an intrinsic property, samples can be compared for relative ee % purity in the absence of external standards. The ratio of ($\phi'+\omega'/2\omega$)×(phase of $\phi'+\omega'$) is linearly related to changes in the Verdet constant of the sample relative to the solvent and independent of light intensity fluctuations from the light source. Thus, the Verdet constant measurement can be utilized to track concentration but the researcher also advantageously obtains the additional information of the analyte's Verdet constant relative to the carrier fluid giving additional specificity over a simply concentration measure.

The system response of an exemplary modified MOPED apparatus according to an embodiment of the invention was simulated in a computer program called MAPLE SOFT 9.0 distributed by Maplesoft of Waterloo, Ontario in Canada. This simulated embodiment used published constants for the enantiomers of lactic acid and water to investigate which inter-modulated sidebands would provide the analytical information necessary for enantiomeric ratio measurements (Surma, M., Molecular Physics, 1999, 96(3) 429-433). Based upon this simulation, FIG. 3 is a table of data showing system response as a function of enantiomeric ratio values according to an embodiment of the present invention.

Figure 3:
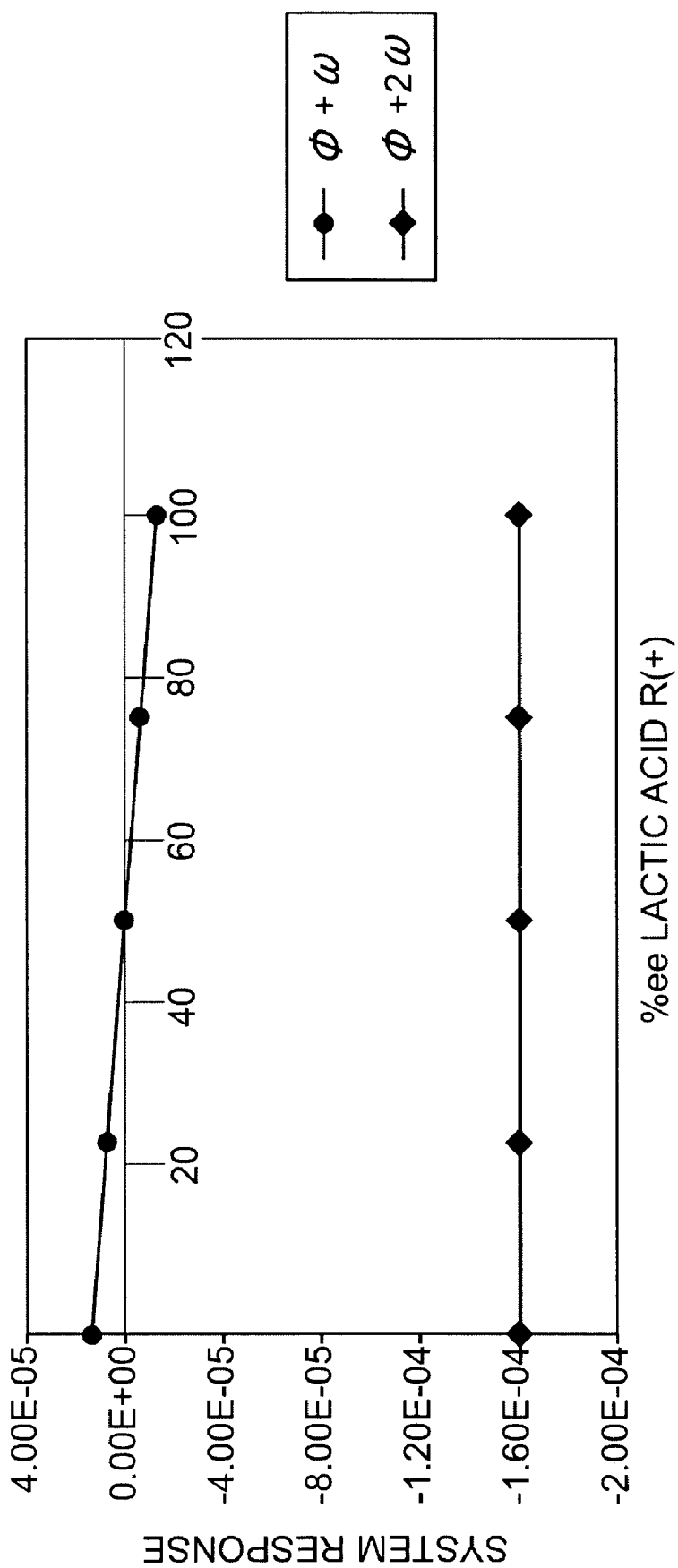
FIG. 3 is an exemplary table of data showing system response as a function of enantiomeric ratio values in accordance with an embodiment of the present invention.
Figure 4:
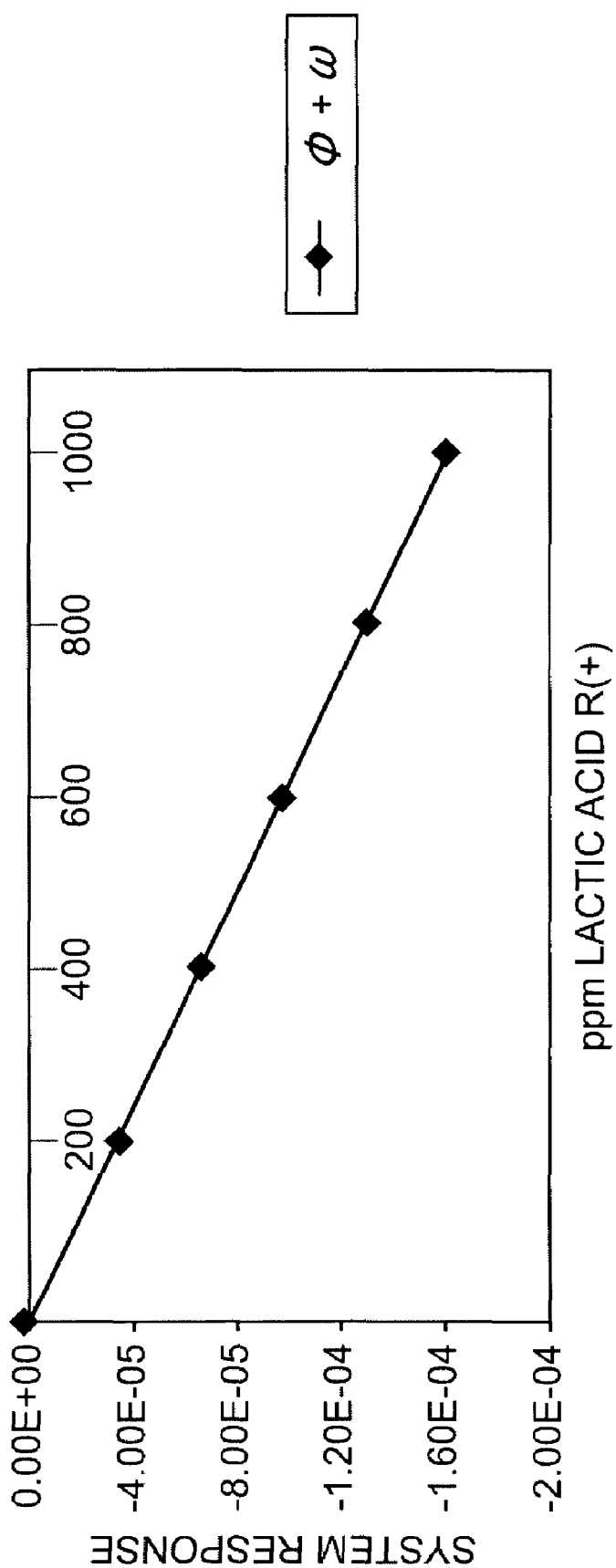
FIG. 4 is an exemplary table of data showing system response as a function of concentration changes in accordance with an embodiment of the present invention.

Referring now to the table of data shown in FIG. 3, the sideband $\phi+\omega$ corresponding to the combination of the fundamental driving frequencies on the Faraday modulator and the sample modulator (in this case $\phi$ and $\omega$ respectively) is invariant when the enantiomeric ratio varies (% R+, lactic acid in this case). However, the same sideband varies linearly with concentration as shown in FIG. 4. The sideband associated with the fundamental sample frequency $\phi$ and the second harmonic of the Faraday modulation $\omega$, is shown to vary linearly with the enantiomeric ratio and crosses zero for a racemic mixture. Therefore, taking the ratio of ($\phi+2\omega)/(\phi+\omega$) yields a signal that is linearly related to the enantiomeric ratio of the sample.

In addition, a ratio measurement provides an additional degree of noise cancellation for system noise. Because this ratio measures an intrinsic property, those skilled in the art will quickly appreciate that one can compare samples for relative ee % purity when standards are not available (e.g., highest ratio has the highest ee %). Other sidebands of the system may also contain useful information, such as the $\phi-\omega$ and $\phi-2\omega$ signals and weaker higher order terms (e.g., $2\phi+2\omega$). The sign of the enantiomer is determined (i.e., levo or dextrorotatory) by the relative phase of the side-band to the internal reference wave use for dual reference digital lock-in analysis.

The exemplary system response shown in FIGS. 3 and 4 is defined by the following equation $$\text{Detector Output }(V) = \text{System Response }(1/W)*$$
$$\text{Throughput Power }(W)*\text{Detector Responsivity }(A/W)*$$
$$\text{Detector Impedance }(V/A \text{ or ohms})*\text{Gain}$$

Figure 9:
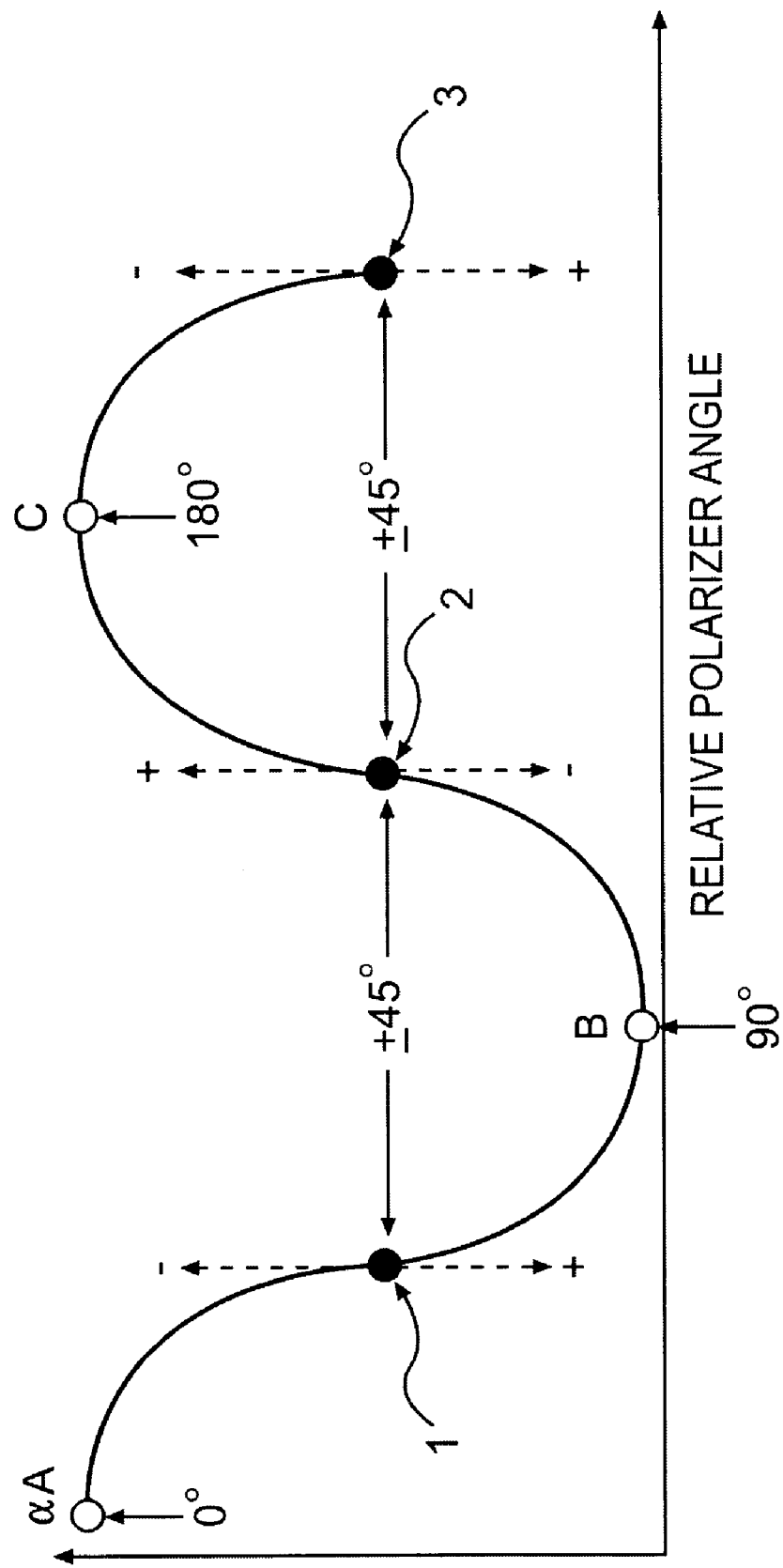
FIG. 9 is an exemplary chart of modulation, such as Faraday modulation, in contrast to relative polarization angle in accordance with an embodiment of the present invention.

In a first example where for the data in the plots of 1000 ppm concentration of lactic acid (88% in water), the typical Si photodiode Responsivity=0.4 A/W, our expected throughput power=0.01 W, commercial photoreceiver Detector Impedance=100 ohms, and the Gain is set as being selectable. So for 25% ee R lactic acid at 1000 ppm, Faraday modulation of ±40 degrees from null (see point B in FIG. 9 that references a similar figure from U.S. Provisional Patent Application Ser. No. 60/510,209 entitled "Differential Optical Technique for Chiral Analysis"), the simulated system response is 1.6e−4 (1/W) for 1000 ppm (1.6e−7(1/W) for 1 ppm). Using these values gives 1.6e−7*0.01*0.4*100*Gain=64 nV*Gain for 1 ppm of lactic acid. As digital lock-in can readily detect signals in the nV range and electronic gain can be applied to the detector output prior to the lock-in, those skilled in the art will appreciate that ppm sensitivity for chiral molecules is readily attainable for such MOPED measurements.

Figure 5:
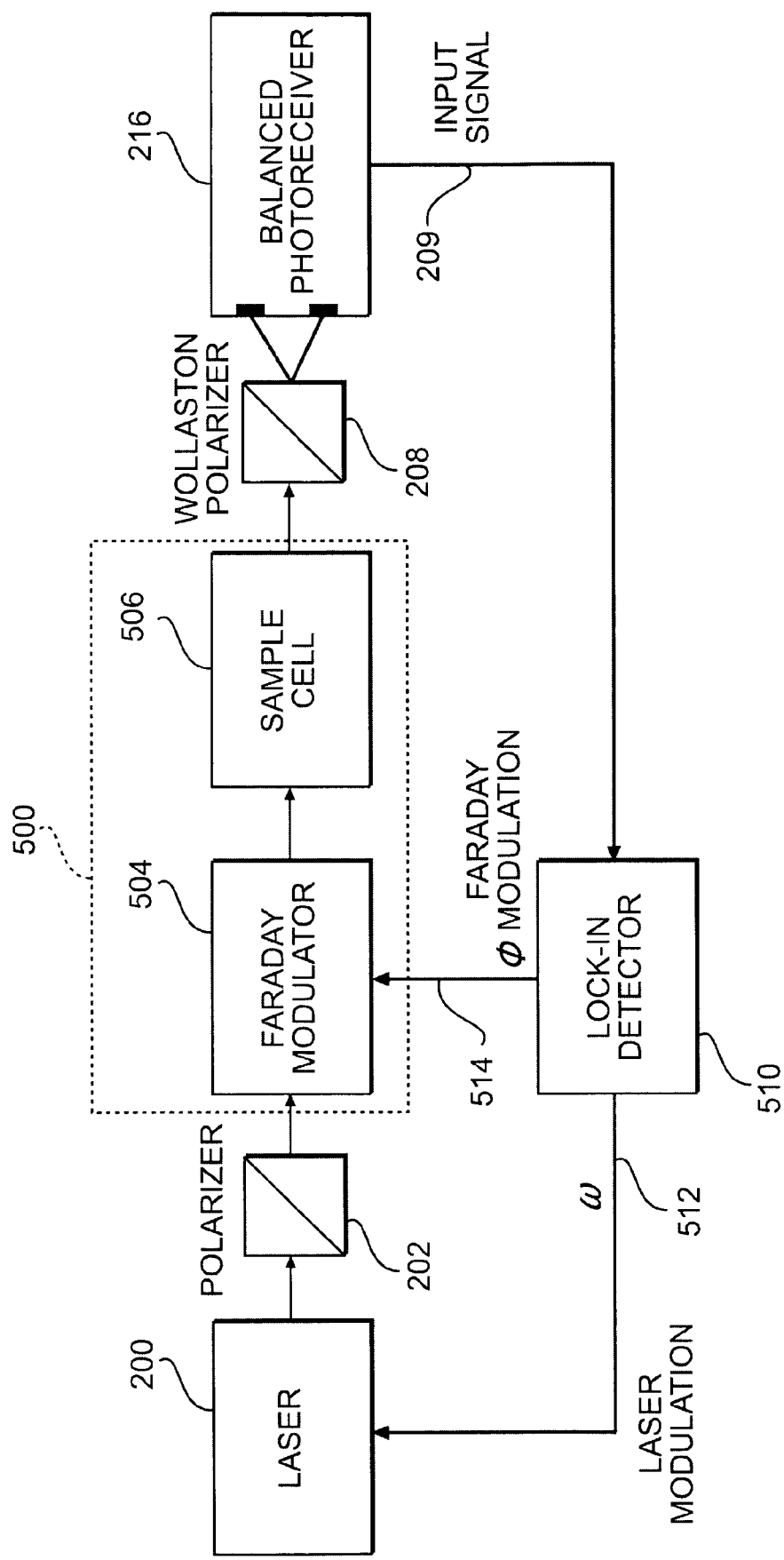
FIG. 5 is an exemplary chiroptical heterodyne apparatus in accordance with an embodiment of the present invention.

Another example of a chiroptical heterodyne system or apparatus according to an embodiment of the present invention is shown in FIG. 5. Referring now to the example illustrated in FIG. 5, the laser 200 is intensity modulated before polarization at polarizer 202 and the modulated chiroptical system is implemented as the faraday modulator 204 and the sample cell 206 (dotted box 500). It is contemplated that the laser 200 may modulated with a variety of signals, including but not limited to sinusoidal signals, a square wave, or a pulse. In the illustrated embodiment, the Faraday modulator 204 is preferably modulated sinusoidally as a resonant circuit. If waveforms other than a sinusoid are utilized when modulating either the laser 200 or the Faraday modulator 204, care should be taken that the harmonic content sidebands do not overlap analytical signal frequencies. Therefore, the laser intensity is modulated and the chiroptical system (such as system 500) is comprised of the faraday modulator 204 and the sample cell 206.

Heterodyne Polarimeter

The embodiment shown in FIG. 5 utilizes a balanced photodetector 216 as a detector. As a result, the common mode signal due to the laser modulation can be efficiently rejected. However, those skilled in the art will appreciate that other detectors, such as a single-ended detector, could also be utilized.

The polarizers 202 and 208 are normally set to the null position (e.g, position B in FIG. 9 on one arm of the Wollaston polarizer 208) and the fundamental signal at the fundamental frequency $\phi$ from the Faraday modulator 204 disappears as noted previously (note label $\phi$ and $\omega$ in FIG. 5). At the null position, the detected signal at $\phi$ is zero. However, the detected signals at $2\phi$ and $2\phi+\omega$ are nonzero and depend upon laser intensity. Furthermore, $\omega$ is zero when a balanced detection scheme is utilized so that the detected signal at the additive inter-modulated sidebands of $\phi+\omega$ will be zero if no chiral species are present in the sample cell.

Those skilled in the art will appreciate that noise pickup at the fundamental often hampers efforts to satisfy the $\phi=0$ null criteria of previous systems. Thus, the system can be more effectively nulled utilizing the $\phi+\omega=0$ criteria due to the noise rejection by observing at sidebands. In addition, the weak optical signal normally observed at $\phi$ is amplified (achieving optical gain) by the large modulation of the laser intensity $\omega$. Dependence of the system upon laser drift, scattering, absorption, and long term output intensity fluctuations may also be normalized by dividing the $\phi+\omega$ signal with the $2\phi+\omega$.

As previously mentioned, the lower or subtractive inter-modulation sidebands may also be utilized but in general the higher frequencies (i.e., the additive inter-modulated sidebands) are generally desired for 1/f noise rejection utilizing the lock-in detector. However, one killed in the art will appreciate that in some embodiments where unwanted intermediate frequencies appear closer to these higher frequencies, it may be desired to use of the lower or subtractive inter-modulation sidebands (e.g., w−f and w−2f or $\phi-\omega$ and $\phi-2\omega$ depending upon the modulation signal labels).

This is an improvement over previous systems which only utilized a constant light source and a single frequency modulation applied to the Faraday modulator and systems utilizing just the 2+harmonic signal to normalize intensity fluctuations.

Heterodyne Circular Dichroism Detector

Another chiral property of interest is circular dichroism (CD). This phenomenon occurs when an absorptive center is in electronic contact with a chiral center and is manifested as a preferential absorption of one circularly polarized waveform (e.g., left circularly polarized). In contrast to polarimetery, which is normally performed at a fixed or narrowband wavelength, CD measurements require a broadband light source in order to optimize the input wavelength for the maximum CD signal. This can be performed with an acousto-optical tunable filter (AOTF) which can rapidly select a wavelength over its tuning range and also independently modulate the transmitted intensity.

Figure 6:
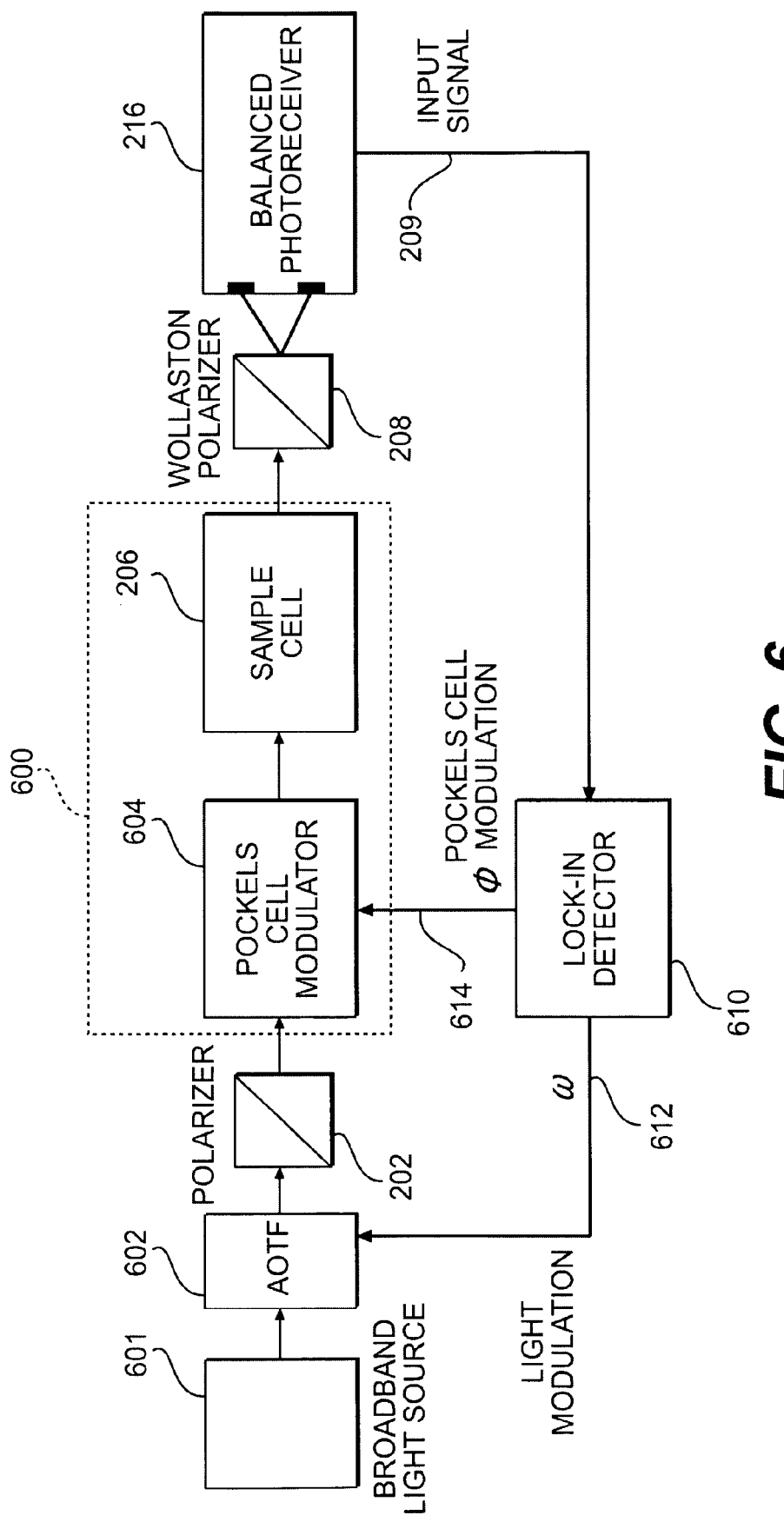
FIG. 6 is a diagram illustrating another exemplary chiroptical heterodyne apparatus having an acousto-optical tunable filter (AOTF), which is utilized to select the input wavelength and modulate the input intensity from a broadband light source.

FIG. 6 is a diagram illustrating an acousto-optical tunable filter, such as AOTF 602, which is utilized to select the input wavelength and modulate the input intensity from broadband light source 601. The light intensity/wavelength is modulated by the AOTF 602 and the chiroptical system 600 is comprised of a Pockels cell modulator 604 and a sample cell 606. The Pockels cell 604 is utilized to modulate the phase of the input linearly polarized light alternating between fully right circularly polarized light and left circularly polarized light (elliptically polarized in between) when the Pockels cell 604 is driven with quarter wave voltages 614. Those skilled in the art will appreciate that the Pockels cell 604 is capable of very high modulation rates ($2.5\times10^{10}$ Hz), but in practice the modulation rate may be limited to those that yield frequencies suitable for the lock-in analysis.

In the example shown in FIG. 6, the light modulation due to modulating signal $\omega$ 612 is effectively cancelled as common mode noise with balanced detection. The modulation of the input circular polarization is equally split between the two detectors in photoreceiver 216 at the applied quarter wave voltages (r-cpl and l-cpl). Thus, the signal at $\phi$ is effectively canceled and a $2\phi$ signal appears similar to the polarimetery case. When a CD active species is present in the sample cell a signal reappears at $\phi$ and $\phi+\omega$. The signal at $2\phi+\omega$ is dependent only on transmitted light intensity and can be utilized to normalize the light fluctuations from the input broadband source 601 yielding the g-factor which is an intrinsic property related to the chiral purity of the species. The $2\phi+\omega$ inter-modulation signal may also be utilized to measure the concentration of the species if the extinction coefficient at the measuring wavelength is known. At high concentrations where the majority of light is absorbed, additional electronic amplification of the signal prior to lock-in analysis may be desired.

Heterodyne Kerr Constant Detector

Figure 7:
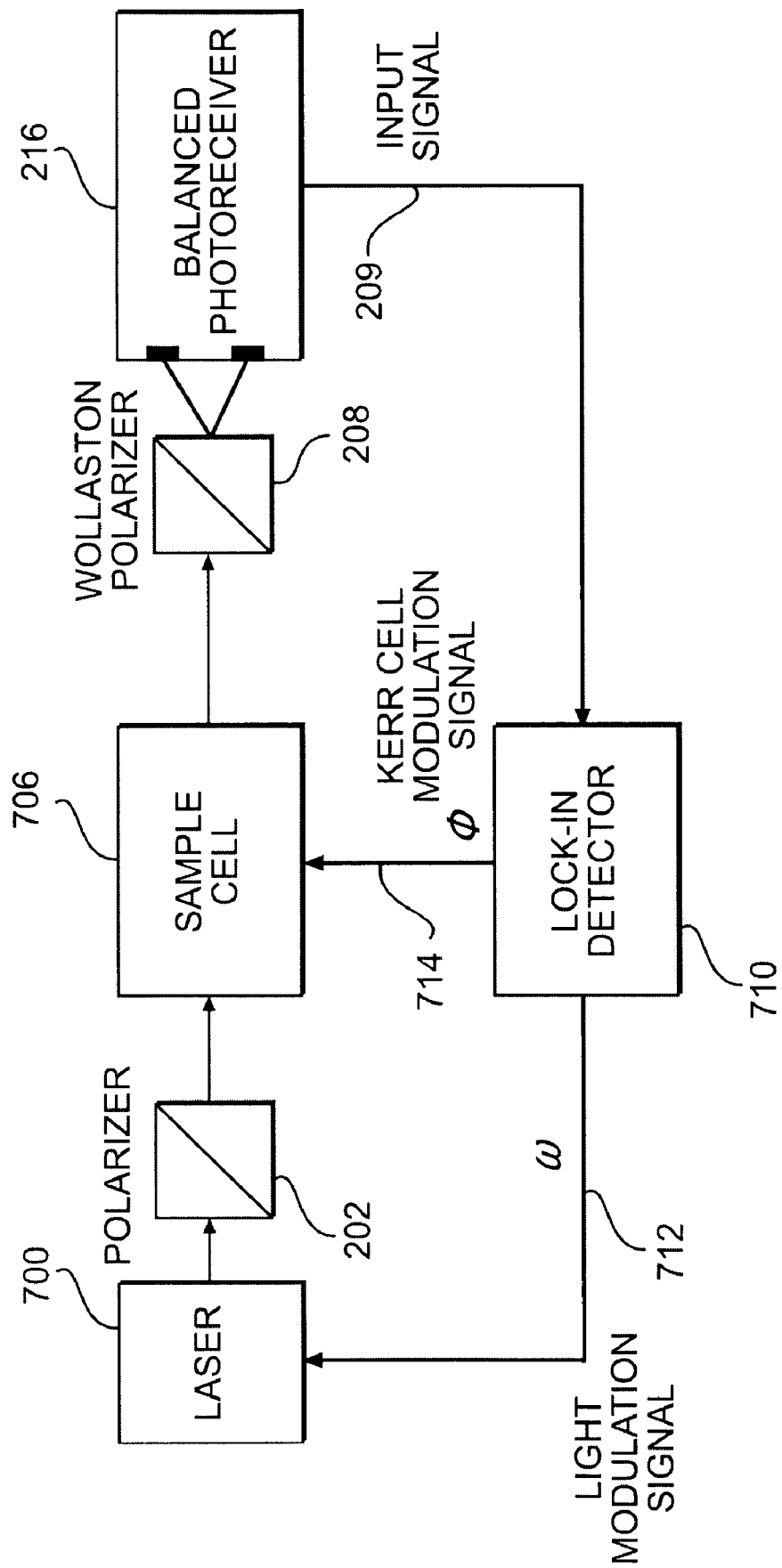
FIG. 7 is a diagram illustrating yet another exemplary chiroptical heterodyne apparatus with light amplitude modulation coupled with sample modulation and which utilizes the electo-optical phenomenon of the Kerr effect in accordance with an embodiment of the present invention.

FIG. 7 is a diagram illustrating an exemplary chiroptical apparatus with light amplitude modulation coupled with sample modulation and which utilizes the electo-optical phenomenon of the Kerr effect in accordance with an embodiment of the present invention. Referring now to FIG. 7, the laser light input intensity is modulated directly and the sample is modulated in an electric field with a Kerr cell setup (electric field perpendicular to light beam). The chiroptical system is comprised of the Kerr cell direct modulation of the sample cell.

The Kerr effect scales as the square of the applied electric field and effectively acts as a variable waveplate on the polarization state on the transmitted light. One advantage of the Kerr cell is the ability to achieve high modulation frequencies ($1\times10^{10}$ Hz). Because lasers are also capable of high modulation rates, one may also take advantage of the subtractive sidebands to down modulate measurements for lock-in analysis when two high frequency modulations are applied. This can be an advantage as compared to Faraday modulation schemes where high frequency modulations are difficult to obtain. In addition utilization of the subtractive sidebands can allow simple low pass filtering to narrow the input bandwidth, allowing more signal gain to be applied prior to lock-in analysis.

Heterodyne Cotton-Mouton Constant Detector

Figure 8:
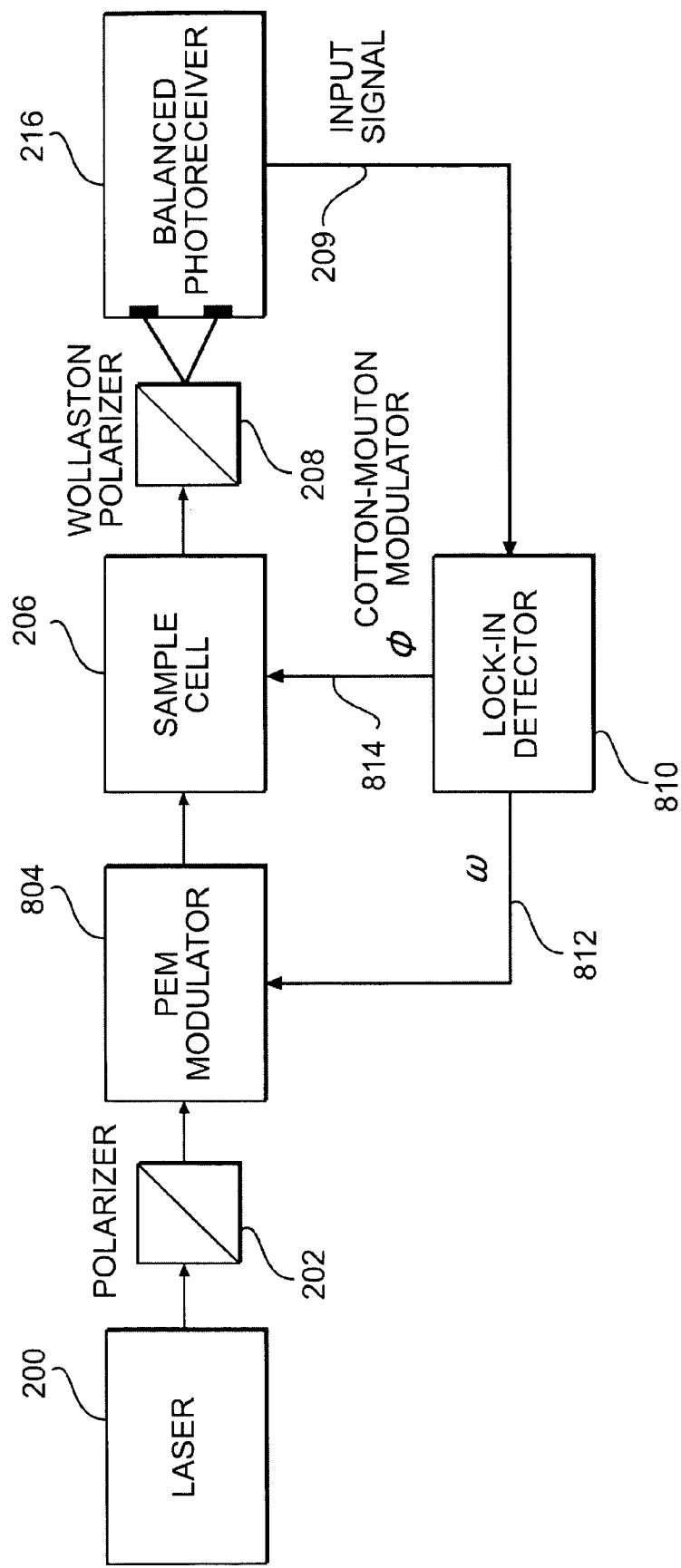
FIG. 8 is a diagram illustrating an still another exemplary chiroptical heterodyne apparatus with light polarization modulation coupled with sample modulation using the Cotton-Mouton effect in accordance with an embodiment of the present invention.

FIG. 8 is a diagram illustrating an exemplary chiroptical apparatus with light polarization state modulation coupled with sample modulation and which utilizes the Cotton-Mouton effect (i.e., a magnetic analog of the Kerr effect) in accordance with an embodiment of the present invention. Referring now to FIG. 8, the Cotton-Mouton effect is utilized to modulate the sample cell 206 and the input light polarization state is modulated by signal 812 via the photoelastic effect utilizing a photoelastic modulator (PEM) 804. A PEM 804 can be utilized to modulate either the linear state or circular polarization state of the input light. In this illustrated embodiment, the PEM is utilized as a linear polarization state modulator because the Cotton-Mouton effect is a linear state polarization effect. The laser light input intensity is modulated directly and the sample is modulated in an electric field with a Kerr cell setup (electric field perpendicular to light beam) related to the sample cell 206. The light intensity/wavelength from laser 700 may be modulated by a acousto-optical tunable filter (not shown).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for detecting a chiral property of a sample, comprising:
    generating a light beam modulated at a first modulation frequency $\omega$;
    modulating the light beam at a second modulation frequency $\phi$, the modulated light beam being transmitted through the sample;
    receiving the modulated light beam at a non-linear photo-detector; and
    analyzing at least one inter-modulation sideband frequency from the mixed output of the non-linear photo-detector to determine the chiral property of the sample, wherein the analyzing step further comprises analyzing a ratio of inter-modulated sideband levels.

2. The method of claim 1, wherein the receiving step further comprises receiving the modulated light beam by an analyzing polarizer that provides a split beam from the modulated light beam to the non-linear photo-detector.

3. The method of claim 1, wherein the receiving step further comprises receiving the modulated light beam by an analyzing polarizer that provides a first portion of the modulated light beam to a first detector in the non-linear photo-detector and that provides a second portion of the modulated light beam to a second detector in the non-linear photo-detector, wherein the first detector and the second detector operate as a balanced photoreceiver.

4. The method of claim 3, wherein the frequency $\omega$ of a first modulation signal and the frequency $\phi$ of a second modulation signal are synchronized with a frequency reference of a lock-in detector receiving the output of the photoreceiver.

5. The method of claim 4, wherein the first modulation signal is a large optical modulation signal and the second modulation signal is a weaker chiroptical signal of interest.

6. The method of claim 1 further comprising, before receiving step, nulling the first portion of the modulated light beam and the second portion of the modulated light beam so that fundamental frequency contributions from the first modulation signal and second modulation signal are reduced for the analyzing step.

7. The method of claim 6, wherein the analyzing step further comprises selectively analyzing the at least one inter-modulation sideband frequency at one or more of a series of additive inter-modulated sidebands.

8. The method of claim 7, wherein the analyzing step further comprises selectively analyzing the at least one inter-modulation sideband frequency at the additive inter-modulated sideband at frequency $\phi+\omega$.

9. The method of claim 7, wherein the analyzing step further comprises selectively analyzing the at least one inter-modulation sideband frequency at the additive inter-modulated sideband at frequency $\phi+2\omega$.

10. The method of claim 6, wherein the analyzing step further comprises selectively analyzing the at least one inter-modulation sideband frequency at one or more of a series of subtractive inter-modulated sidebands.

11. The method of claim 1, wherein the ratio of inter-modulated sideband levels $(\phi+2\omega)/(\phi+\omega)$ is analyzed yielding a signal that is linearly related to the chiral property of the sample.

12. The method of claim 11, wherein the chiral property of the sample is an enantiomeric ratio of the sample.

13. An apparatus for measuring a chiroptical property of a sample, comprising:
    a first modulator that imparts a first modulation onto a probe beam of light at a frequency of $\omega$;
    a second modulator that imparts a second modulation onto the probe beam of light at a frequency of $\phi$, the modulated probe beam of light being transmitted through the sample;
    an analyzing polarizer that receives the modulated probe beam after the second modulator and provides a split beam to a non-linear photo-detector; and
    the non-linear photo-detector that mixes the first modulation with the second modulation to analyze frequency components at inter-modulated sidebands, the level of the inter-modulated sidebands being related to the chiroptical property of the sample.

14. The apparatus of 13, wherein the first modulator imparts an optical modulation on the probe beam.

15. The apparatus of claim 14, wherein the second modulator imparts a system polarization modulation on the probe beam.

16. The apparatus of claim 13, wherein the non-linear photo-detector further comprises:
    a first detector that receives a first portion of the split beam; and
    a second detector that receives a second portion of the split beam.

17. The apparatus of claim 16, wherein the non-linear photo-detector having the first detector and the second detector is a balanced photoreceiver.

18. The apparatus of claim 13 further comprising a lock-in detector for receiving a signal output from the non-linear photo-detector and generating modulation signals for the first modulator and the second modulator.

19. The apparatus of claim 18, wherein the frequency $\omega$ of the first modulation signal and the frequency $\phi$ of the second modulation signal are synchronized with a frequency reference of the lock-in detector.

20. The apparatus of claim 13, wherein the first modulation signal is a large optical modulation signal and the second modulation signal is a weaker chiroptical signal of interest.

21. The apparatus of claim 13, wherein the non-linear photo-detector is a square law detector.

22. The apparatus of claim 17, wherein the analyzing polarizer is used to null the first portion of the split beam and the second portion of the split beam so that the fundamental frequency contributions from the first modulation signal and second modulation signal are reduced at the photoreceiver.

23. The apparatus of claim 22, wherein the photoreceiver is used to selectively analyze frequency components at additive inter-modulated sidebands.

24. The apparatus of claim 22, wherein the photoreceiver is used to selectively analyze frequency components at the additive inter-modulated sideband at frequency $\phi+\omega$.

25. The apparatus of claim 22, wherein the photoreceiver is used to selectively analyze frequency components at the additive inter-modulated sideband at frequency $\phi+2\omega$.

26. The apparatus of claim 22, wherein the photoreceiver is used to selectively analyze frequency components at subtractive inter-modulated sidebands.

27. The apparatus of claim 13, wherein the non-linear photo-detector is part of a photoreceiver capable of analyzing a ratio of inter-modulated sideband levels.

28. The apparatus of claim 27, wherein the photoreceiver is further capable of analyzing a ratio of ratio of inter-modulated sideband levels $(\phi+2\omega)/(\phi+\omega)$ to yield a signal that is linearly related to the chiral property of the sample.

29. The apparatus of claim 28, wherein the chiral property of the sample is an enantiomeric ratio of the sample.

30. A method for detecting at least one chiral property of an analyte within a sample, comprising:
passing a polarized light beam being modulated at a first modulation frequency $\omega$ through the sample as the sample is exposed to a magnetic field being modulated at a second modulation frequency $\phi$;
nulling at least a portion of a fundamental component of the polarized light beam;
detecting, after nulling at least a portion of the fundamental component of the polarized light beam, at least one inter-modulation sideband frequency from the mixed output of a non-linear photo-detector; and
determining the at least one chiral property of the analyte within the sample based upon a parameter of the detected at least one inter-modulation sideband frequency.

31. The method of claim 30, wherein the parameter is at least one from the group of the amplitude and phase of the detected at least one inter-modulation sideband frequency.

32. The method of 30, wherein the detecting step further comprises detecting the at least one inter-modulation sideband frequency using a plurality of non-linear detectors within a balanced photoreceiver.

33. The method of 30, wherein the at least one inter-modulation sideband frequency is an additive inter-modulated sideband frequency.

34. The method of 33, wherein the at least one inter-modulation sideband frequency is an additive inter-modulated sideband frequency at $\phi+\omega$.

35. The method of 33, wherein the at least one inter-modulation sideband frequency is an additive inter-modulated sideband frequency at $\phi+2\omega$.

36. The method of 30, wherein the at least one inter-modulation sideband frequency is a subtractive inter-modulated sideband frequency.

37. The method of 30, wherein the determining step further comprises analyzing a ratio of the levels from a plurality of additive inter-modulated sideband frequencies.

38. The method of 30, wherein the determining step further comprises analyzing a ratio of the levels from a plurality of additive inter-modulated sideband frequencies of $(\phi+2\omega)/(\phi+\omega)$ to yield a signal that is linearly related to the chiral property of the sample.

39. An apparatus for measuring a chiroptical property of a sample, comprising:
a first modulation signal source generating a first modulation signal at a frequency $\omega$;
a second modulation signal source generating a second modulation signal at a frequency $\phi$;
a light source coupled to the first modulation signal source, the light source being modulated by the first modulation signal to provide a probe beam;
a Faraday modulator coupled to the second modulation signal source, the Faraday modulator being capable of receiving the probe beam to impart additional modulation on the probe beam in response to the second modulation signal;
a sample cell coupled to the output of the Faraday modulator for receiving the probe beam and exposing the sample within the sample cell to the probe beam; and
a non-linear photo-detector that detects at least one inter-modulated sideband associated with the frequency $\omega$ of the first modulation signal and the frequency $\phi$ of the second modulation signal, the level of the at least one inter-modulated sideband being related to the chiroptical property of the sample.

40. An apparatus for measuring a chiroptical property of a sample, comprising:
a first modulation signal source generating a first modulation signal at a frequency $\omega$;
a second modulation signal source generating a second modulation signal at a frequency $\phi$;
a broadband light source providing a probe beam;
an acousto-optical tunable filter receiving the probe beam and capable of modulating the probe beam based upon the first modulation signal;
a Pockels Cell modulator coupled to the second modulation signal source, the Pockels Cell modulator being capable of receiving the probe beam to impart additional modulation on the probe beam in response to the second modulation signal;
a sample cell coupled to the output of the Pockels Cell modulator for receiving the probe beam and exposing the sample within the sample cell to the probe beam; and
a non-linear photo-detector that detects at least one inter-modulated sideband associated with the frequency $\omega$ of the first modulation signal and the frequency $\phi$ of the second modulation signal, the level of the at least one inter-modulated sideband being related to the chiroptical property of the sample.

41. An apparatus for measuring a chiroptical property of a sample, comprising:
a first modulation signal source generating a first modulation signal at a frequency $\omega$;
a second modulation signal source generating a second modulation signal as a Kerr Cell modulation signal at a frequency $\phi$;
a light source coupled to the first modulation signal source, the light source being modulated by the first modulation signal to provide a probe beam;
a sample cell coupled to the Kerr Cell modulation signal, the sample cell being capable of receiving the probe beam to impart additional modulation on the probe beam in response to the second modulation signal while exposing the sample within the sample cell to the probe beam; and
a non-linear photo-detector that detects at least one inter-modulated sideband associated with the frequency $\omega$ of the first modulation signal and the frequency $\phi$ of the second modulation signal, the level of the at least one inter-modulated sideband being related to the chiroptical property of the sample.

42. An apparatus for measuring a chiroptical property of a sample, comprising:
a first modulation signal source generating a first modulation signal at a frequency $\omega$;

a second modulation signal source generating a second modulation signal as a Cotton-Mouton modulation signal at a frequency $\phi$;

a light source to provide a probe beam;

a Faraday modulator coupled to the first modulation signal, the Faraday modulator being capable of receiving the probe beam to impart modulation on the probe beam in response to the first modulation signal;

a sample cell coupled to the Cotton-Mouton modulation signal, the sample cell being capable of receiving the probe beam to impart additional modulation on the probe beam in response to the Cotton-Mouton modulation signal while exposing the sample within the sample cell to the probe beam; and a non-linear photo-detector that detects at least one inter-modulated sideband associated with the frequency $\omega$ of the first modulation signal and the frequency $\phi$ of the second modulation signal, the level of the at least one inter-modulated sideband being related to the chiroptical property of the sample.

* * * * *

UNITED STATES PATENT AND TRADEMARK OFFICE
CERTIFICATE OF CORRECTION

PATENT NO. : 7,405,826 B2  Page 1 of 1
APPLICATION NO. : 11/168295
DATED : July 29, 2008
INVENTOR(S) : Phillip R. Gibbs et al.

It is certified that error appears in the above-identified patent and that said Letters Patent is hereby corrected as shown below:

In claim 14, column 12, line 29, "of 13," should read --of claim 13,--.

In claim 28, column 13, line 11, "a ratio of ratio of inter-modulated" should read --a ratio of inter-modulated--.

In claim 32, column 13, line 35, "of 30," should read --of claim 30,--.

In claim 33, column 13, line 39, "of 30," should read --of claim 30,--.

In claim 34, column 13, line 42, "of 33," should read --of claim 33,--.

In claim 35, column 13, line 45, "of 33," should read --of claim 33,--.

In claim 36, column 13, line 48, "of 30," should read --of claim 30,--.

In claim 37, column 13, line 51, "of 30," should read --of claim 30,--.

In claim 38, column 13, line 54, "of 30," should read --of claim 30,--.

In claim 39, column 14, line 10, "ωof" should read --ω of--.

Signed and Sealed this

Twenty-first Day of October, 2008

JON W. DUDAS
*Director of the United States Patent and Trademark Office*